United States Patent [19]
Hawkins et al.

[11] Patent Number: 5,840,544
[45] Date of Patent: Nov. 24, 1998

[54] DNA ENCODING RANTES HOMOLOG FROM PROSTATE

[75] Inventors: Phillip R. Hawkins; Olga Bandman, both of Mountain View; Lynn E. Murry, Portalo Valley, all of Calif.

[73] Assignee: Incyte Pharmaceuticals, Inc., Palo Alto, Calif.

[21] Appl. No.: 633,682

[22] Filed: Apr. 17, 1996

[51] Int. Cl.⁶ .............................. C12P 21/02; C12N 15/19
[52] U.S. Cl. .................... 435/69.5; 435/172.3; 435/375; 536/23.5
[58] Field of Search .......................... 536/23.5; 435/69.5, 435/172.3, 375

[56] References Cited

U.S. PATENT DOCUMENTS 5,605,817  2/1997  Coleman et al. ..................... 435/69.5

OTHER PUBLICATIONS

Bacon et al., "Activation of Dual T Cell Signaling Pathways by the Chemokine RANTES", *Science*, 269:1727–1729 (1995).
Blum et al., "Three Human Homologs of a Murine Gene Encoding an Inhibitor of Stem Cell Proliferation", *DNA and Cell Biology*, 9(8):589–602, (1990).
Callard et al., *The Cytokine Facts Book*, Academic Press, San Diego, CA, pp. 226–227, 180–187 (1994).
Covell et al., "Analysis of Hydrophobicity in the α and β chemokine families and its relevance to dimerization," *Protein Science*, 3:2064–72 (1994).
Meurer et al., *J. Exp. Med.*, 178:1913–1921 (1993).
Schall et al., "A Human T Cell–Specific Molecule Is A Member of a New Gene Family", *The Journal of Immunology*, 141(3):1018–1025, (1988).
Shin et al., "Definition of a Lipopolysaccharide–Responsive Element in the 5'–Flanking Regions of MuRantes and crg–2", *Molecular and Cellular Biology*, 14(5):2914–2925.

*Primary Examiner*—Stephen Walsh
*Assistant Examiner*—Daryl A. Basham
*Attorney, Agent, or Firm*—Incyte Pharmaceuticals; Lucy J. Billings; Barbara J. Luther

[57] ABSTRACT

The present invention provides a polynucleotide PTEC (prostate expressed chemokine) isolated from a prostate cDNA library which identifies and encodes a novel human rantes homolog PTEC (prostate expressed chemokine). The invention provides for genetically engineered expression vectors and host cells comprising the nucleic acid sequence encoding PTEC. The invention also provides for the therapeutic use of purified PTEC in the treatment of immune deficiency diseases, and for the therapeutic use of antisense molecules, antibodies, antagonists or inhibitors in the treatment of conditions or diseases associated with the expression of PTEC. The invention also describes diagnostic assays which utilize diagnostic compositions comprising the polynucleotide, or fragments thereof, or antibodies which specifically bind to the polypeptide.

5 Claims, 8 Drawing Sheets

```
                                         9                    18                27                36                45                54
5' ATG GGC CTC TCC TTG GCC TCT GCT GTG CTC CTG GCC TCC CTC CTG AGT CTC CAC
   M   G   L   S   L   A   S   A   V   L   L   A   S   L   L   S   L   H 63                72                81                90                99               108
   CTT GGA ACT GCC ACA CGT GGG AGT GAC ATA TCC AAG ACC TGC TTC CAA TAC
   L   G   T   A   T   R   G   S   D   I   S   K   T   C   F   Q   Y 117               126               135               144               153               162
   AGC CAC AAG CCC CTT CCC TGG ACC TGG GTG CGA AGC TAT GAA TTC ACC AGT AAC
   S   H   K   P   L   P   W   T   W   V   R   S   Y   E   F   T   S   N 171               180               189               198               207               216
   AGC TGC TCC CAG CGG GCT GTG ATA TTC ACT ACC AAA AGA GGC AAG AAA GTC TGT
   S   C   S   Q   R   A   V   I   F   T   T   K   R   G   K   K   V   C 225               234               243               252               261               270
   ACC CAT CCA AGG AAA AAA TGG GTG CAA AAA TAC ATT TCT TTA CTG AAA ACT CCG
   T   H   P   R   K   K   W   V   Q   K   Y   I   S   L   L   K   T   P

279
   AAA CAA TTG TGA   3'
   K   Q   L
```

FIGURE 1

```
1   MGLSLAS--AVLLASLLHLGTATRGSDISKTCCFQYSH              836820.PTEC
1   MKISAAALTIILTAAALCTPAPASPYGSD-TTPCCFAYLS             mouse rantes
1   MKVSAARLAVILIATALCAPASASPYSSD-TTPCCFAYIA             human rantes
1   MQVSTAALAVLLCTMALCNQFSASLAADT-PTACCFSYTS             mip-1alpha 39  KPLPWTWVRSYEFTSNSCSQRAVIFTTKRGKKVCTHPRKK             836820.PTEC
40  LALPRAHVKEYFYTSSKCSNLAVVFVTRRNRQVCANPEKK             mouse rantes
40  RPLPRAHIKEYFYTSGKCSNPAVVFVTRKNRQVCANPEKK             human rantes
40  RQIPQNFIADYFETSSQCSKPGVIFLTKRSRQVCADPSEE             mip-1alpha 79  WVQKYISLLKTPKQL                                       836820.PTEC
80  WVQEYINYLEMS                                          mouse rantes
80  WVREYINSLEMS                                          human rantes
80  WVQKYVSDLELSA                                         mip-1alpha
```

Decoration 'Decoration #1': Box residues that differ from 836820.PTEC.

FIGURE 2

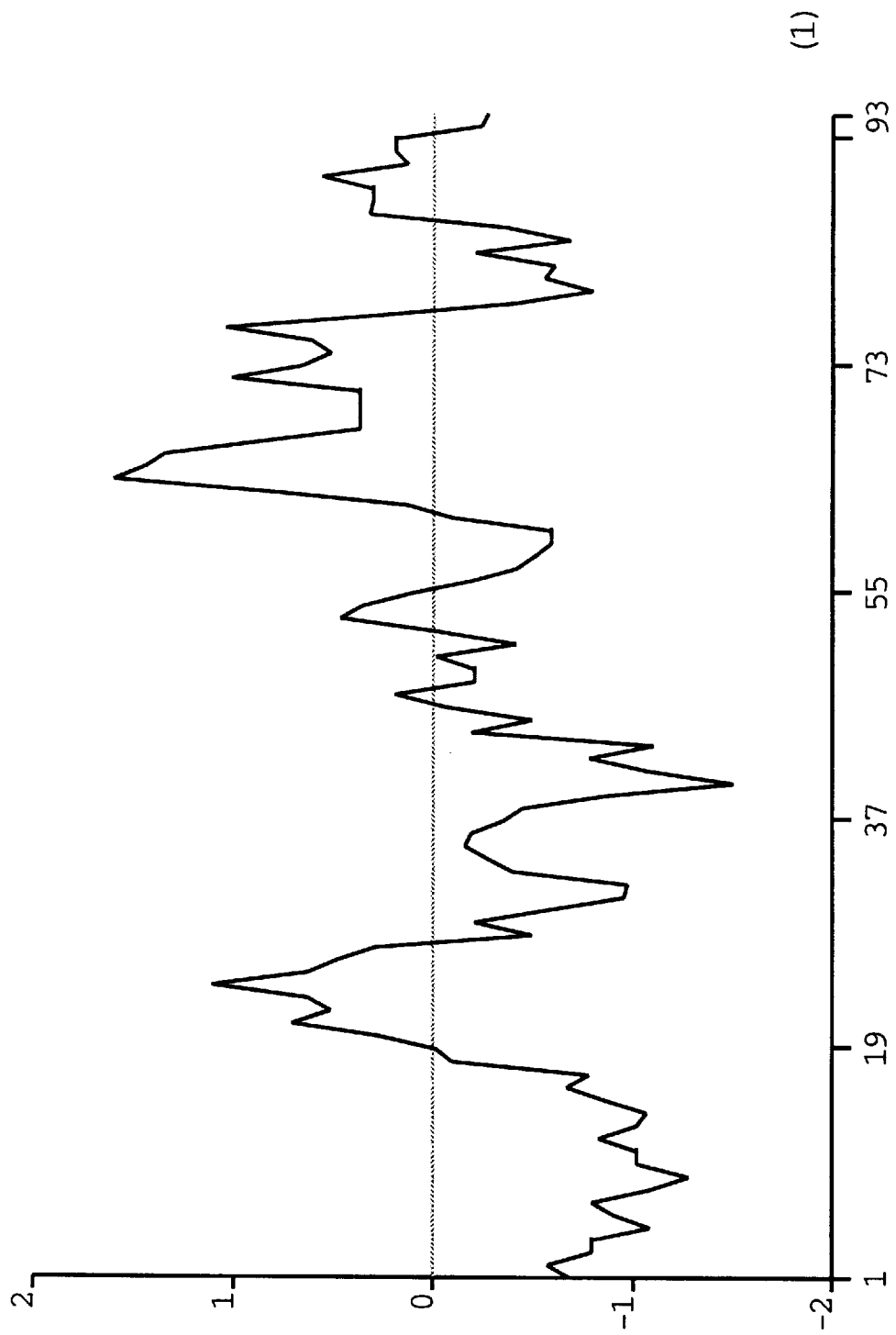
FIGURE 3A (1)

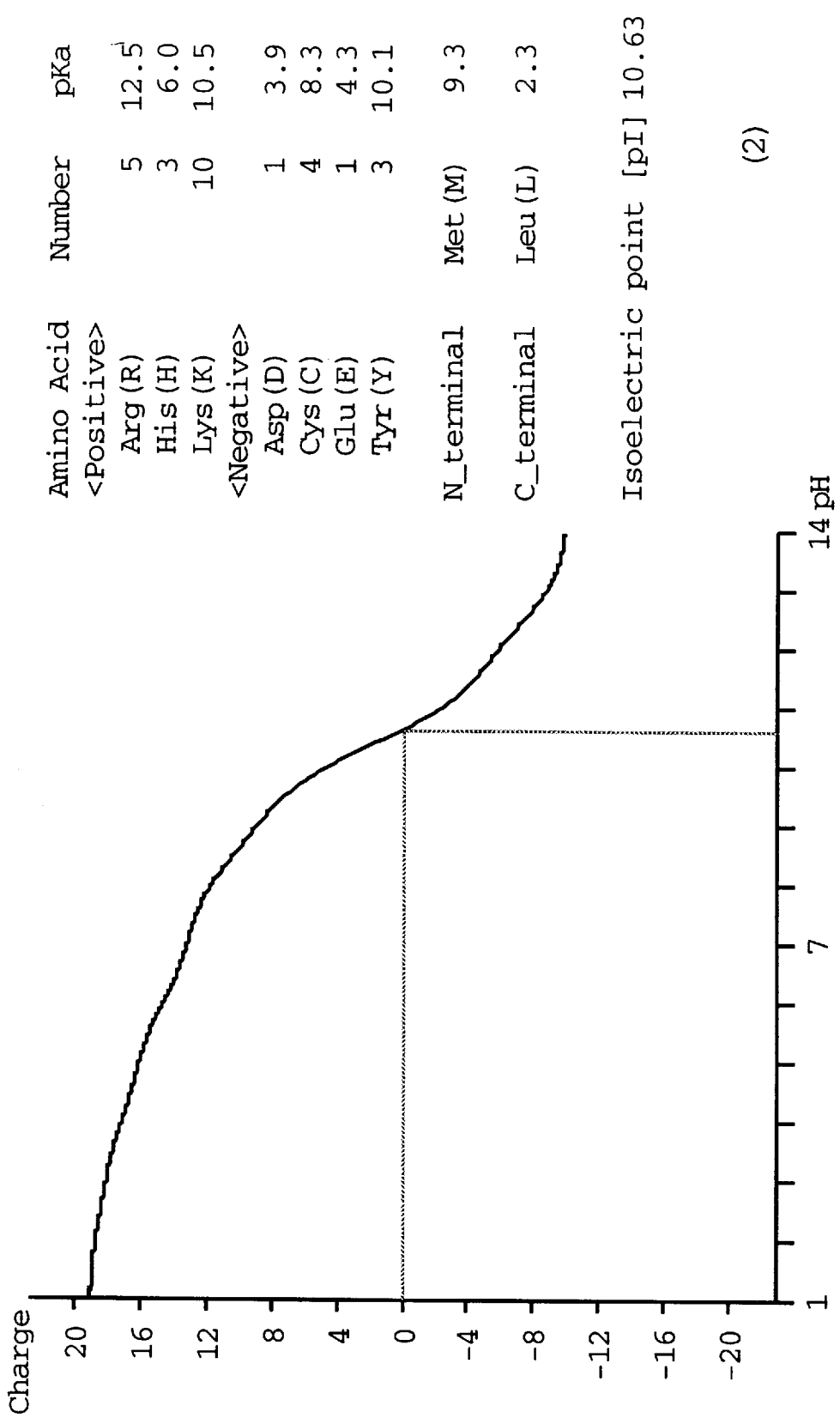
FIGURE 3A (2)

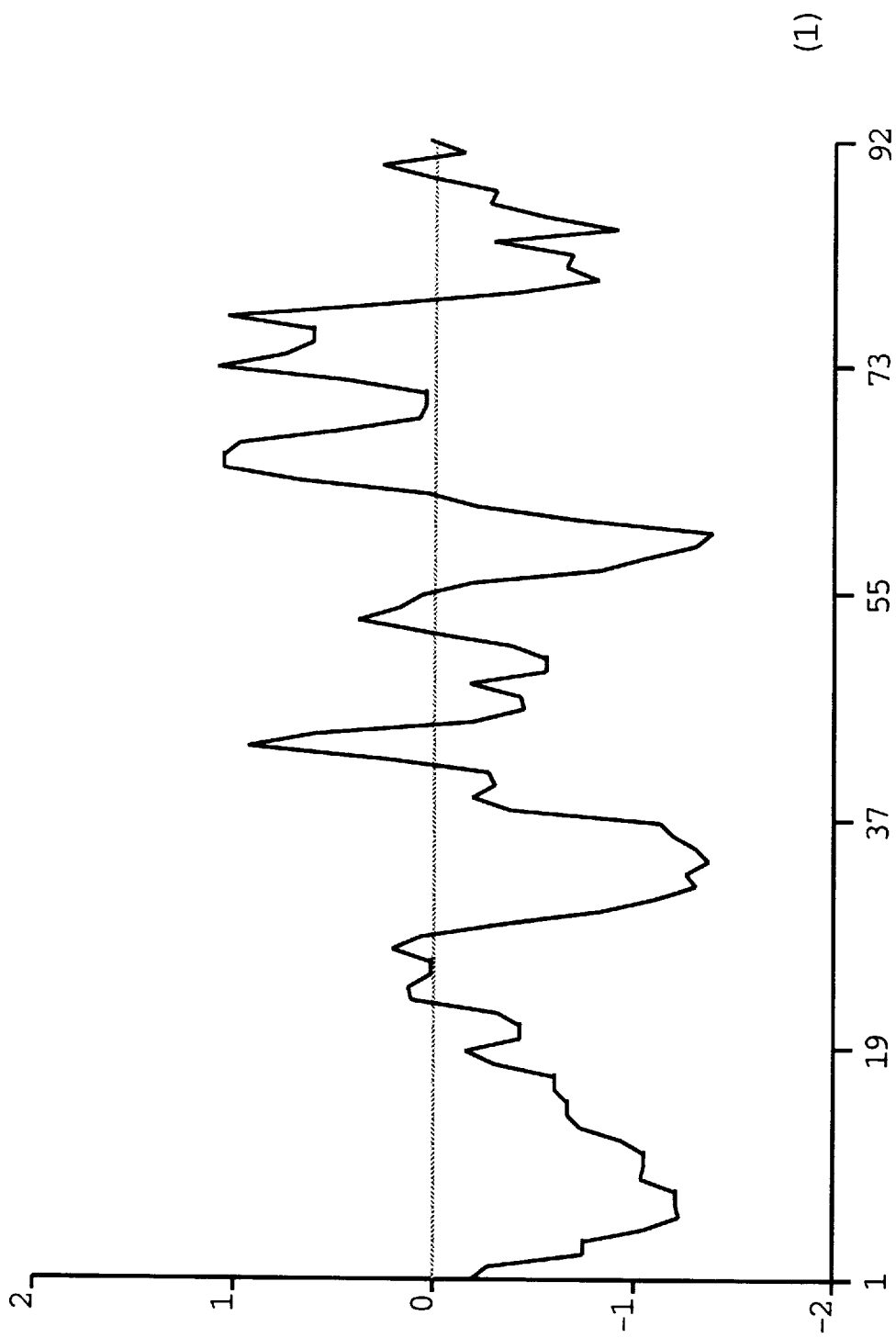

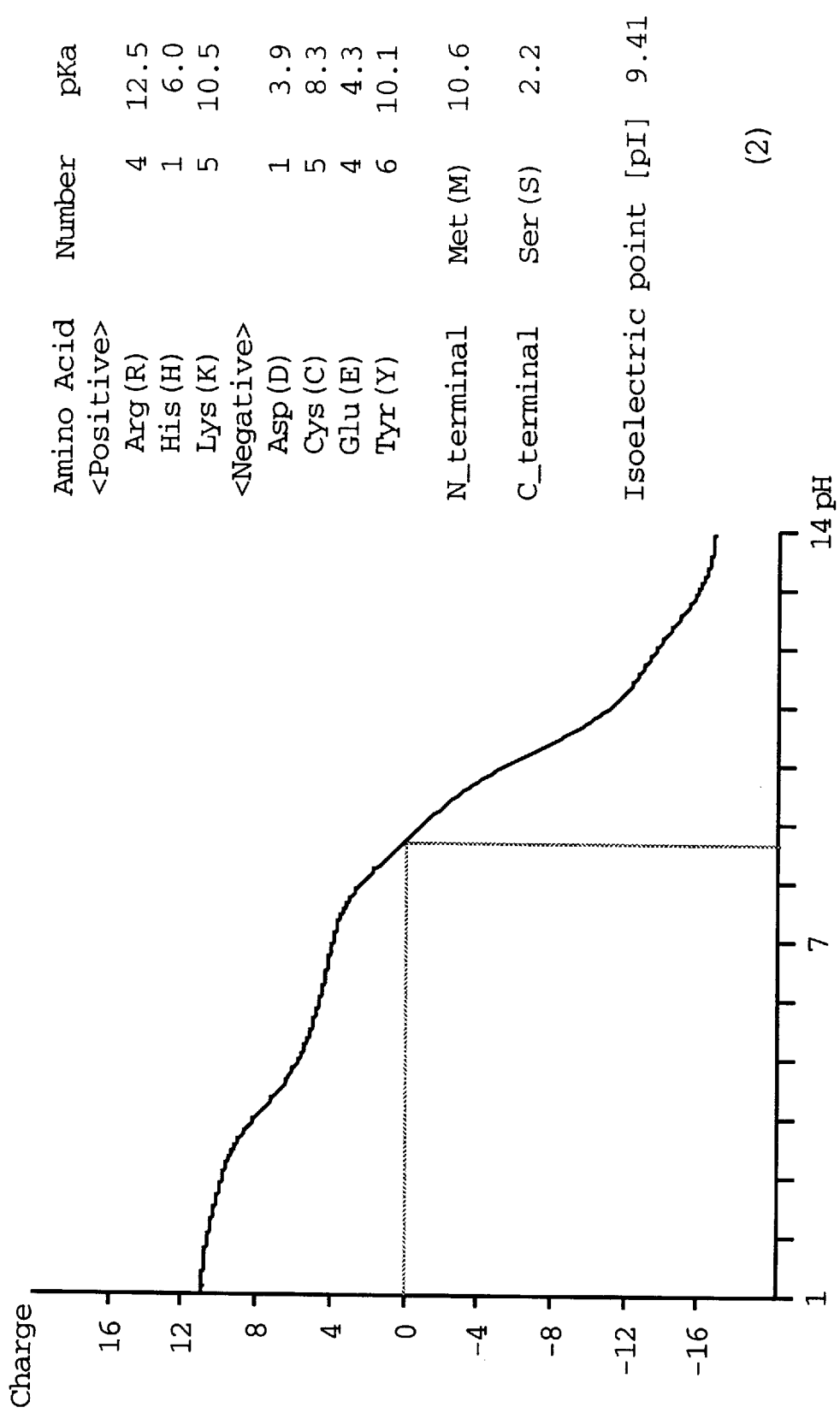
FIGURE 3B (2)

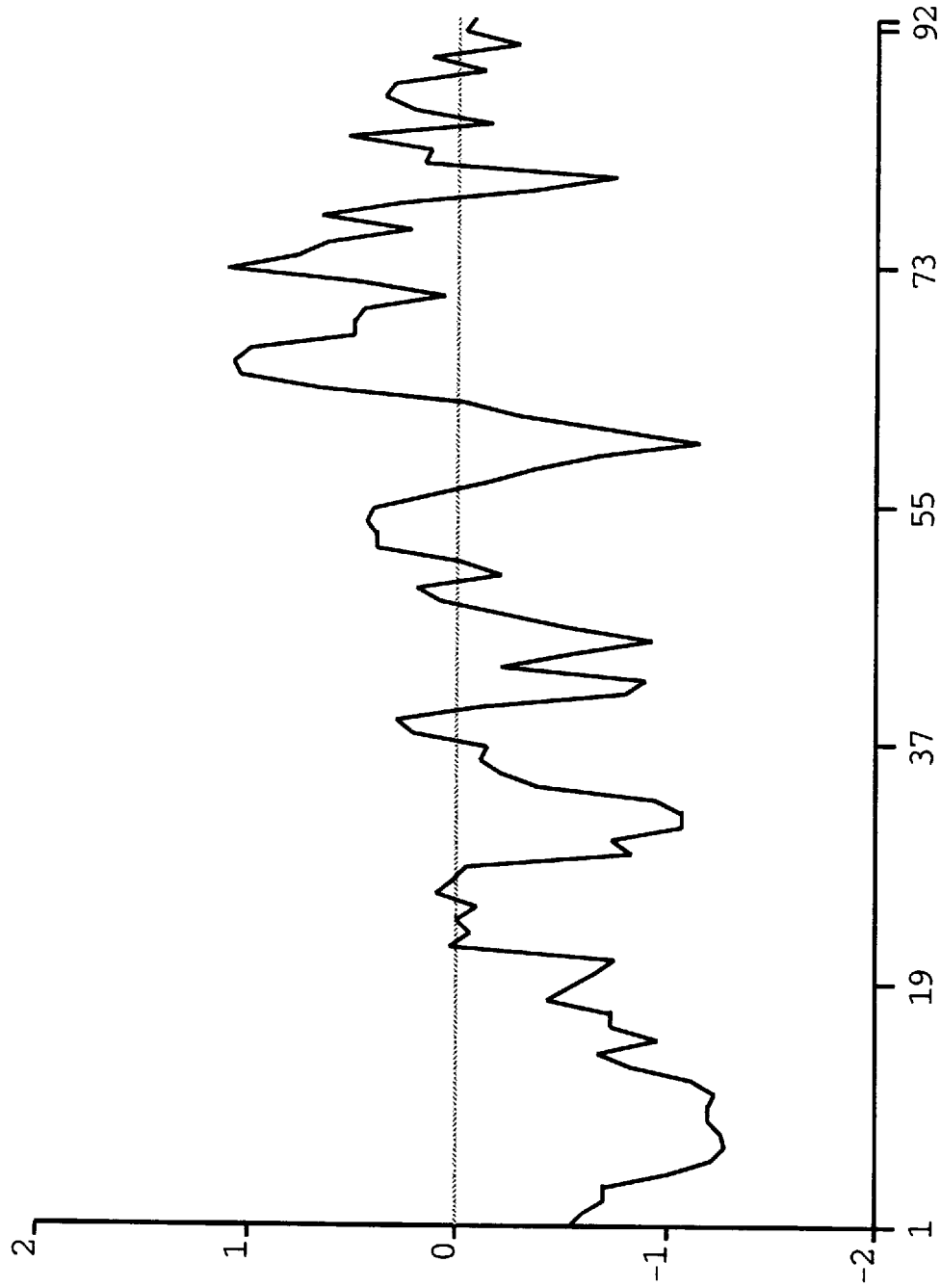
FIGURE 3C (1)

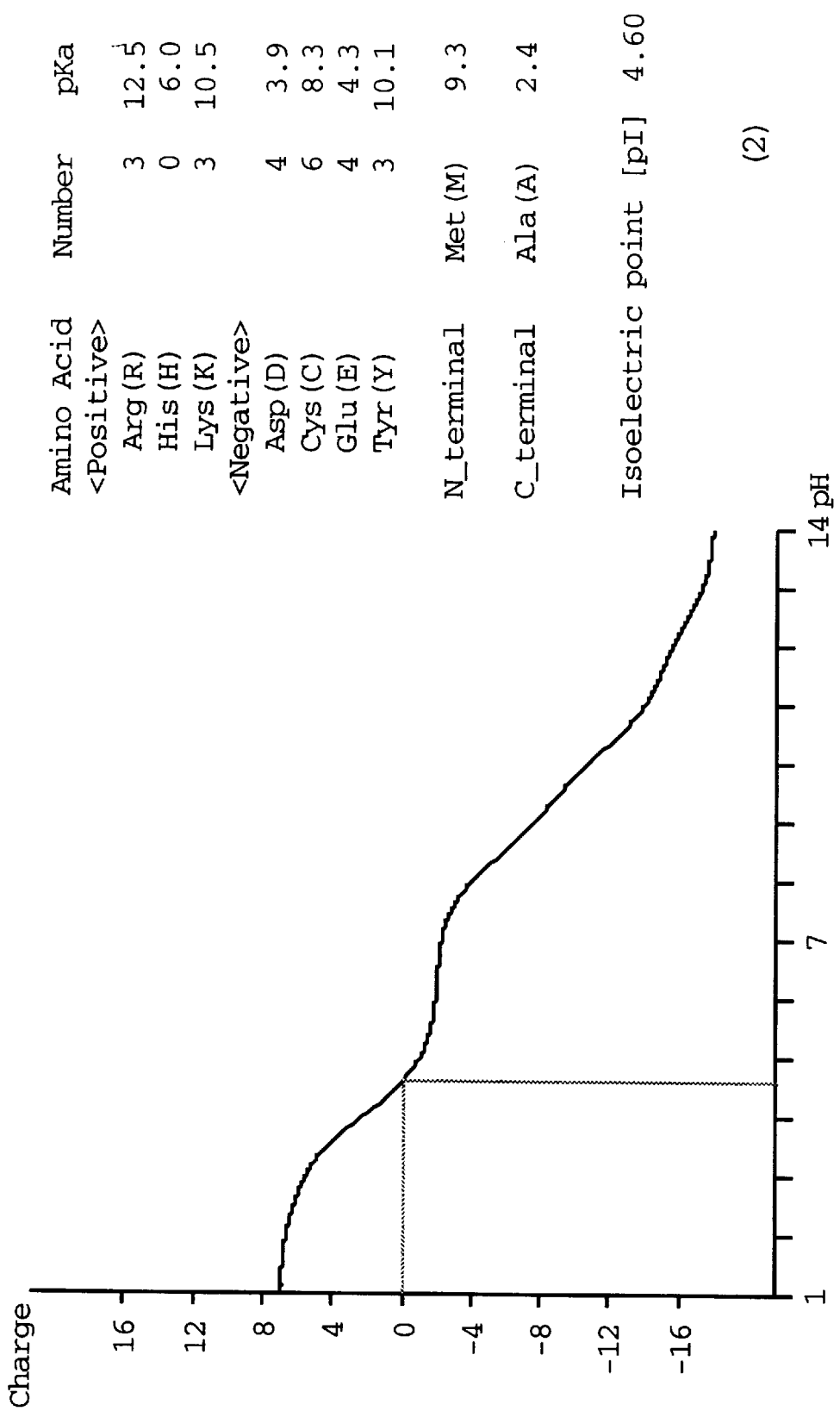
FIGURE 3C (2)

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 570 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Prostrate
        ( B ) CLONE: 836820

( x i ) SEQUENCE DESCRIPTION: SEQ ID NO:1:

| | | | | | | |
|---|---|---|---|---|---|---|
| GCCAAGCTCT | AATACGACTC | ACTATAGGGA | AAGCTGGTAC | GCCTGCAGGT | ACCGGTCCGG | 60 |
| AATTCCCGGG | TCGACCCACG | CGTCCGAGGG | CCTGATTTGC | AGCATCATGA | TGGGCCTCTC | 120 |
| CTTGGCCTCT | GCTGTGCTCC | TGGCCTCCCT | CCTGAGTCTC | CACCTTGGAA | CTGCCACACG | 180 |
| TGGGAGTGAC | ATATCCAAGA | CCTGCTGCTT | CCAATACAGC | CACAAGCCCC | TTCCCTGGAC | 240 |
| CTGGGTGCGA | AGCTATGAAT | TCACCAGTAA | CAGCTGCTCC | CAGCGGGCTG | TGATATTCAC | 300 |
| TACCAAAAGA | GGCAAGAAAG | TCTGTACCCA | TCCAAGGAAA | AAATGGGTGC | AAAAATACAT | 360 |
| TTCTTTACTG | AAAACTCCGA | AACAATTGTG | ACTCAGCTGA | ATTTCATCC | GAGGACGCTT | 420 |
| GGACCCCGCT | CTTGGCTCTG | CAGCCCTCTG | GGGAGCCTGC | GGAATCTTTT | CTGAAGGCTA | 480 |
| CATGGACCCG | CTGGGGAGGA | GAGGGTGTTT | CCTCCCAGAG | TTACTTTAAT | AAAGGTTGTT | 540 |
| CATAGAGTTG | AAAAAAAAAA | AAAAAAAAA | | | | 570 |

( 2 ) INFORMATION FOR SEQ ID NO:2:

( i ) SEQUENCE CHARACTERISTICS:
        ( A ) LENGTH: 93 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: Prostrate
        ( B ) CLONE: 836820

( x i ) SEQUENCE DESCRIPTION: SEQ ID NO:2:

| Met | Gly | Leu | Ser | Leu | Ala | Ser | Ala | Val | Leu | Leu | Ala | Ser | Leu | Leu | Ser |
|---|---|---|---|---|---|---|---|---|---|---|---|---|---|---|---|
| 1 | | | | 5 | | | | | 10 | | | | | 15 | |
| Leu | His | Leu | Gly | Thr | Ala | Thr | Arg | Gly | Ser | Asp | Ile | Ser | Lys | Thr | Cys |
| | | | 20 | | | | | 25 | | | | | 30 | | |

```
         Cys  Phe  Gln  Tyr  Ser  His  Lys  Pro  Leu  Pro  Trp  Thr  Trp  Val  Arg  Ser
                   35                      40                      45

Tyr  Glu  Phe  Thr  Ser  Asn  Ser  Cys  Ser  Gln  Arg  Ala  Val  Ile  Phe  Thr
              50                      55                      60

Thr  Lys  Arg  Gly  Lys  Lys  Val  Cys  Thr  His  Pro  Arg  Lys  Lys  Trp  Val
         65                      70                      75                           80

Gln  Lys  Tyr  Ile  Ser  Leu  Leu  Lys  Thr  Pro  Lys  Gln  Leu
                             85                      90
```

( 2 ) INFORMATION FOR SEQ ID NO:3:

( i ) SEQUENCE CHARACTERISTICS:
        ( A ) LENGTH: 91 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: GI 134510

( x i ) SEQUENCE DESCRIPTION: SEQ ID NO:3:

```
         Met  Lys  Val  Ser  Ala  Ala  Arg  Leu  Ala  Val  Ile  Leu  Ile  Ala  Thr  Ala
         1                        5                       10                      15

Leu  Cys  Ala  Pro  Ala  Ser  Ala  Ser  Pro  Tyr  Ser  Ser  Asp  Thr  Thr  Pro
                             20                      25                      30

Cys  Cys  Phe  Ala  Tyr  Ile  Ala  Arg  Pro  Leu  Pro  Arg  Ala  His  Ile  Lys
                   35                      40                      45

Glu  Tyr  Phe  Tyr  Thr  Ser  Gly  Lys  Cys  Ser  Asn  Pro  Ala  Val  Val  Phe
              50                      55                      60

Val  Thr  Arg  Lys  Asn  Arg  Gln  Val  Cys  Ala  Asn  Pro  Glu  Lys  Lys  Trp
         65                      70                      75                           80

Val  Arg  Glu  Tyr  Ile  Asn  Ser  Leu  Glu  Met  Ser
                             85                      90
```

( 2 ) INFORMATION FOR SEQ ID NO:4:

( i ) SEQUENCE CHARACTERISTICS:
        ( A ) LENGTH: 92 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: GI 182847

( x i ) SEQUENCE DESCRIPTION: SEQ ID NO:4:

```
         Met  Gln  Val  Ser  Thr  Ala  Ala  Leu  Ala  Val  Leu  Leu  Cys  Thr  Met  Ala
         1                        5                       10                      15

Leu  Cys  Asn  Gln  Phe  Ser  Ala  Ser  Leu  Ala  Ala  Asp  Thr  Pro  Thr  Ala
                             20                      25                      30

Cys  Cys  Phe  Ser  Tyr  Thr  Ser  Arg  Gln  Ile  Pro  Gln  Asn  Phe  Ile  Ala
                   35                      40                      45

Asp  Tyr  Phe  Glu  Thr  Ser  Ser  Gln  Cys  Ser  Lys  Pro  Gly  Val  Ile  Phe
              50                      55                      60

Leu  Thr  Lys  Arg  Ser  Arg  Gln  Val  Cys  Ala  Asp  Pro  Ser  Glu  Glu  Trp
         65                      70                      75                           80
```

-continued

```
Val  Gln  Lys  Tyr  Val  Ser  Asp  Leu  Glu  Leu  Ser  Ala
               85                       90
```

(2) INFORMATION FOR SEQ ID NO:5:

(i) SEQUENCE CHARACTERISTICS:
  (A) LENGTH: 91 amino acids
  (B) TYPE: amino acid
  (C) STRANDEDNESS: single
  (D) TOPOLOGY: linear (ii) MOLECULE TYPE: peptide (vii) IMMEDIATE SOURCE:
  (A) LIBRARY: GenBank
  (B) CLONE: GI 475206

(xi) SEQUENCE DESCRIPTION: SEQ ID NO:5:

```
Met  Lys  Ile  Ser  Ala  Ala  Ala  Leu  Thr  Ile  Ile  Leu  Thr  Ala  Ala  Ala
 1               5                        10                       15

Leu  Cys  Thr  Pro  Ala  Pro  Ala  Ser  Pro  Tyr  Gly  Ser  Asp  Thr  Thr  Pro
               20                       25                       30

Cys  Cys  Phe  Ala  Tyr  Leu  Ser  Leu  Ala  Leu  Pro  Arg  Ala  His  Val  Lys
               35                       40                       45

Glu  Tyr  Phe  Tyr  Thr  Ser  Ser  Lys  Cys  Ser  Asn  Leu  Ala  Val  Val  Phe
      50                       55                       60

Val  Thr  Arg  Arg  Asn  Arg  Gln  Val  Cys  Ala  Asn  Pro  Glu  Lys  Lys  Trp
 65                      70                       75                       80

Val  Gln  Glu  Tyr  Ile  Asn  Tyr  Leu  Glu  Met  Ser
               85                       90
```

DNA ENCODING RANTES HOMOLOG FROM PROSTATE

FIELD OF THE INVENTION

The present invention relates to nucleic acid and amino acid sequences of a novel rantes homolog from prostate and to the use of these sequences in the diagnosis, study, prevention and treatment of disease.

BACKGROUND OF THE INVENTION

The chemokines are small polypeptides, generally about 70–100 amino acids (aa) in length, 8–11 kD in molecular weight, and active over a 1–100 ng/ml concentration range. Initially, chemokines were isolated and purified from inflamed tissues and characterized relative to their bioactivity. More recently, chemokines have been discovered through molecular cloning techniques and characterized by structural as well as functional analysis. Closely related polypeptides currently assigned to the β chemokine family also display definitive spacing of the first two cysteine residues in the mature molecule and act on a diverse group of target cells, many of which are leukocytes and include monocytes and macrophages, basophils, eosinophils, and T lymphocytes. The known chemokines and their functions are reviewed by Schall TJ (1994; *Chemotactic Cytokines: Targets for Therapeutic Development,* International Business Communications, Southborough, Mass., pp 180–270) and by Paul WE (1993; *Fundamental Immunology,* Raven Press, New York, N.Y., pp 822–26).

Relatively few C—C chemokines have been fully described, but they are clearly distinct from the α or C-X-C chemokines and the γ or C chemokines. Although both α and β chemokines generally function as dimers, the β chemokines appear to have less N-terminal processing. Known C—C chemokines include the macrophage chemotactic proteins (MCP), macrophage inflammatory proteins (MIP), I-309, TCA3, and RANTES.

Monocyte chemotactic protein (MCP-1) is a 76 amino acid mature protein which appears to be expressed in almost all cells and tissues upon stimulation by a variety of agents. According to Charo I, personal communication the targets of MCP-1 may be limited to monocytes and basophils in which it induces an mcp-1 receptor:G protein-linked calcium flux. Two other related proteins (MCP-2 and MCP-3) have been purified from a human osteosarcoma cell line. MCP-2 and MCP-3 have 62% and 73% amino acid identity, respectively, with MCP-1 and both share MCP-1's chemoattractant specificity for monocytes.

MIP-1α and MIP-1β were first purified from a stimulated mouse macrophage cell line and elicited an inflammatory response when injected into normal tissues. At least three distinct and non-allelic genes encode human MIP-1α, and seven genes, MIP-1β. MIP-1α and MIP-1β consist of 68–69 amino acids which are about 70% identical in their acidic, mature secreted forms. They are both expressed in stimulated leukocytes, particularly T cells, B cells and monocytes in response to mitogens, anti-CD3 and endotoxin, and both polypeptides bind heparin. While both molecules stimulate monocytes, MIP-1α chemoattracts the CD-8 subset of T lymphocytes and eosinophils, while MIP-1β chemoattracts the CD-4 subset of T lymphocytes. In mouse, these proteins are known to stimulate myelopoiesis.

I-309 was cloned from a human γ-δ T cell line and shows 42% amino acid identity to T cell activation gene 3 (TCA3) cloned from mouse. There is considerable nucleotide homology between the 5' flanking regions of these two proteins, and they share an extra pair of cysteine residues not found in other chemokines. Such similarities suggest I-309 and TCA3 are species homologs which have diverged over time in both sequence and function.

RANTES is a C—C chemokine with structural similarity to the interleukin-8 (IL-8) and human MIP-1β (Covell DG et al. (1994) Protein Science 3:2064–72). It is expressed by T lymphocytes and macrophages and has been identified in some tumor cell lines and in rheumatoid synovial fibroblasts. Both human and murine forms of the 68 amino acid mature protein are known; they share 85% homology and some cross reactivity. The human gene is located on chromosome 17q11–q21.

RANTES expression can be stimulated using LPS, and it is regulated by interleukins-1 and -4, transforming nerve factor and interferon-γ. The cDNA cloned from T cells encodes a basic 8 kD protein which lacks N-linked glycosylation and may or may not have O-linked glycosylation.

RANTES functions through the mobilization of calcium ions ($Ca^{++}$; Meurer R et al. (1993) J Exp Med 178:1913–1921). When the heterotrimeric G-protein coupled receptors are involved, chemotaxis of monocytes, memory helper T cells (but not B cells), and eosinophils occurs. When protein tyrosine kinases are involved, cellular responses such as channel opening, interleukin 2 receptor expression, cytokine release and T cell proliferation occur (Bacon KB et al. (1995) Science 269:1727–29). RANTES has a different receptor than IL-8 and MIP-1α; however, it can displace MIP-1α from its normal receptor (Callard R and A Gearing (1994) *The Cytokine Facts Book,* Academic Press, San Diego, Calif.).

RANTES also triggers the release of histamine from basophils and mast cells and activates T cells in an antigen-independent manner. Within four hours of intradermal injection in dog; RANTES, IL-8, and MCP-1 resulted in eosinophil and macrophage rich inflammation, neutrophil infiltration, and perivascular cuffing of monocytes, respectively.

The discovery of the novel RANTES homolog disclosed herein presents opportunities to intercede in inflammation, allergies, and asthma attributable to chemotaxis and other cellular responses mediated by such β chemokines.

SUMMARY

The present invention relates to a novel beta (β) chemokine identified among the cDNAs from a prostate library and to the use of the nucleic acid and amino acid sequences of this novel chemokine in the study, diagnosis, prevention and treatment of disease. The novel chemokine of the present invention was first identified within Incyte Clone 836820 through a computer generated search for amino acid sequence alignments. The nucleic acid sequence disclosed herein and designated in lower case, ptec, SEQ ID NO: 1, encodes the amino acid sequence which is designated in upper case PTEC, SEQ ID NO: 2. The present invention is based, in part, on the chemical and structural homology between PTEC and mouse RANTES (GenBank GI 475206; Shin HS et al (1994) Mol Cell Biol 14:2914–25).

PTEC has a length of 93 amino acids, a signal sequence of approximately 22 residues, the definitive cysteine residues of a β chemokine ($C_{32}$–$C_{33}$, $C_{56}$ and $C_{72}$) and an isoelectric point of 10.63. The mature protein has approximately 70% amino acid homology to mouse RANTES (Shin, supra), 68% to human RANTES (GI 134510; Schall TJ et al (1988) J Immunol 141:1018–25), and 67% to MIP-1α (GI 182847; Blum S et al (1990) DNA Cell Biol 9: 589–602).

The nucleic acid sequence, oligonucleotides, fragments, portions or antisense molecules thereof, may be used in diagnostic assays of body fluids or biopsied tissues to detect expression of ptec. For example, ptec sequences can be used to detect the presence of the mRNA transcript in a patient before autoimmune tissue destruction reaches excessive levels or to monitor ptec levels during treatment for inflammation. The nucleic acid sequence also provides for the design of antisense molecules useful in diminishing or eliminating expression of the genomic nucleotide sequence in individuals with overactive immune response, specifically to prevent tissue destruction. The present invention also relates, in part, to the inclusion of the polynucleotide in an expression vector which can be used to transform host cells or organisms. Such transgenic hosts are useful for production and recovery of the encoded PTEC.

The invention further provides diagnostic kits for the detection of naturally occurring PTEC. It provides for the use of purified PTEC as a positive control and to produce antibodies or identify other antagonists or inhibitors which bind PTEC. Anti-PTEC antibodies are useful to monitor PTEC levels in body fluids such as blood or urine or in extracts of biopsied tissues where PTEC is expressed.

The invention further comprises administration of purified PTEC to immuno-compromised individuals for the purpose of inducing leukocyte proliferation. Likewise, antibodies, antagonists or inhibitors can be administered to hyper-responsive individuals to prevent PTEC from attracting monocytes, macrophages, and eosinophils to a particular organ or inflamed site. Such administrations moderate the immune response and preventing excessive secretion or release of proteolytic enzymes which cause unwarranted tissue destruction.

The invention also comprises pharmaceutical compositions containing the polypeptide, antibodies, antagonists or inhibitors. These molecules are useful for the prevention or treatment of conditions such as viral, bacterial, fungal or helminthic infections; allergic or asthmatic responses; mechanical injury associated with trauma; arteriosclerosis, atherogenesis or collagen vascular diseases; autoimmune diseases such as rheumatoid arthritis, myasthenia gravis, systemic lupus erythematosus, or hemolytic anemia; leukemia, lymphomas or carcinomas; immune deficiency diseases such as AIDS, X-linked agammaglobulinemia, ataxia telangiectasia, cirrhosis, cystic fibrosis, diabetes mellitus, hepatitis, and sickle cell anemias, or diseases of immediate type hypersensitivity which involve activation or excessive proliferation of leukocytes, particularly monocytes, macrophages, eosinophils, basophils, mast and T cells.

DESCRIPTION OF THE FIGURES

FIG. 1 displays the nucleic acid sequence (SEQ ID NO:1) and deduced amino acid sequence (SEQ ID NO:2) of the novel RANTES homolog, PTEC, from human prostate. The alignment of the nucleic acid and amino acid sequences were produced using MacDNAsis software (Hitachi Software Engineering Co Ltd).

FIG. 2 shows the amino acid sequence alignment between PTEC (SEQ ID NO:2), mouse RANTES (GenBank GI 475206; Shin HS et al (1994) Mol Cell Biol 14:2914–25), human RANTES (GI 134510; Schall TJ et al (1988) J Immunol 141:1018–25), and MIP-1α (GI 182847; Blum S et al (1990) DNA Cell Biol 9: 589–602). Sequences were aligned using the multisequence alignment program of DNASTAR software (DNASTAR Inc, Madison, Wis.).

FIGS. 3A(1), 3A(2), 3B(1), 3B(2), 3C(1), 3C(2) show the hydrophobicity (1) and isoelectric (2) plots of PTEC, RANTES, and MIP-1α, respectively, produced using MacDNAsis software.

DETAILED DESCRIPTION OF THE INVENTION

The present invention relates to a novel human RANTES homolog whose nucleic acid sequence was identified within Incyte Clone 836820 from a prostate cDNA library (PROSNOT07) and to the use of the polynucleotide (lower case, ptec) and polypeptide (upper case, PTEC) shown in FIG. 1 in the study, diagnosis, prevention and treatment of disease.

PTEC has a length of 93 amino acids, a signal sequence of approximately 22 residues, the definitive cysteine residues of a β chemokine ($C_{32}$–$C_{33}$, $C_{56}$ and $C_{72}$; FIG. 2). The mature protein, those residues beyond the signal sequence, has approximately 70% amino acid homology to mouse RANTES (GenBank GI 475206; Shin HS et al (1994) Mol Cell Biol 14:2914–25) and most closely resembles this molecule in isoelectric properties. The mature PTEC shares amino acid identity with the mature mouse RANTES at residues $G_{25}$–$D_{27}$, $C_{32}$–$F_{34}$, $Y_{36}$, $L_{41}$–$P_{42}$, $V_{46}$, and $Y_{49}$. PTEC displays 68% homology to the mature human RANTES (GI 134510; Schall TJ et al (1988) J Immunol 141:1018–25), and 67% to the mature MIP-1α (GI 182847; Blum S et al (1990) DNA Cell Biol 9: 589–602). Although the hydrophobicity plots of PTEC and MIP-1α appear to parallel one another, it must be noted that the isoelectric points for PTEC and MIP-1α are 10.63 and 4.60, respectively (FIG. 3).

The nucleic acid sequence, oligonucleotides, fragments, portions or antisense molecules thereof, may be used in diagnostic assays of body fluids or biopsied tissues to detect expression of ptec. For example, ptec sequences can be used to detect the presence of the mRNA transcript in a patient before autoimmune tissue destruction reaches excessive levels or to monitor ptec levels during treatment for inflammation. The nucleic acid sequence also provides for the design of antisense molecules useful in diminishing or eliminating expression of the genomic nucleotide sequence in individuals with overactive immune response, specifically to prevent tissue destruction. The present invention also relates, in part, to the inclusion of the polynucleotide in an expression vector which can be used to transform host cells or organisms. Such transgenic hosts are useful for production and recovery of the encoded PTEC.

The invention further provides diagnostic kits for the detection of naturally occurring PTEC. It provides for the use of purified PTEC as a positive control and to produce antibodies or identify other antagonists or inhibitors which bind PTEC. Anti-PTEC antibodies are useful to monitor PTEC levels in body fluids such as blood or urine or in extracts of biopsied tissues where PTEC is expressed.

The invention further comprises administration of purified PTEC to immuno-compromised individuals for the purpose of inducing leukocyte proliferation. Likewise, antibodies, antagonists or inhibitors can be administered to hyper-responsive individuals to prevent PTEC from attracting monocytes, macrophages, and eosinophils to a particular organ or inflamed site. Such administrations moderate the immune response and preventing excessive secretion or release of proteolytic enzymes which cause unwarranted tissue destruction.

The invention also comprises pharmaceutical compositions containing the polypeptide, antibodies, antagonists or inhibitors. These molecules are useful for the prevention or treatment of conditions such as viral, bacterial, fungal or helminthic infections; allergic or asthmatic responses; mechanical injury associated with trauma; arteriosclerosis, atherogenesis or collagen vascular diseases; autoimmune diseases such as rheumatoid arthritis, myasthenia gravis, systemic lupus erythematosus, or hemolytic anemia; leukemia, lymphomas or carcinomas; immune deficiency diseases such as AIDS, X-linked agammaglobulinemia, ataxia telangiectasia, cirrhosis, cystic fibrosis, diabetes mellitus, hepatitis, and sickle cell anemias, or diseases of immediate type hypersensitivity which involve activation or excessive proliferation of leukocytes, particularly monocytes, macrophages, eosinophils, basophils, mast and T cells.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to an oligopeptide, peptide, polypeptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen PE et al (1993) Anticancer Drug Des 8:53–63).

As used herein, PTEC refers to the amino acid sequence of PTEC from any species, particularly mammalian, including bovine, ovine, porcine, murine, equine, and preferably human, in a naturally occurring form or from any source whether natural, synthetic, semi-synthetic or recombinant. As used herein, "naturally occurring" refers to an amino acid sequence which is found in nature.

The present invention also encompasses PTEC variants. A preferred PTEC variant is one having at least 80% amino acid sequence similarity, a more preferred PTEC variant is one having at least 90% amino acid sequence similarity and a most preferred PTEC variant is one having at least 95% amino acid sequence similarity to the PTEC amino acid sequence (SEQ ID NO:2). A "variant" of PTEC may have an amino acid sequence that is different by one or more amino acid "substitutions". The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software.

The term "biologically active" refers to a PTEC having structural, regulatory or biochemical functions of the naturally occurring PTEC. Likewise, "immunologically active" defines the capability of the natural, recombinant or synthetic PTEC, or any oligopeptide thereof, to induce a specific immune response in appropriate animals or cells and to bind with specific antibodies.

The term "derivative" as used herein refers to the chemical modification of a ptec or the encoded PTEC. Illustrative of such modifications would be replacement of hydrogen by an alkyl, acyl, or amino group. A PTEC derivative would encode a polypeptide which retains essential biological characteristics of natural PTEC.

As used herein, the term "purified" refers to molecules, either nucleic or amino acid sequences, that are removed from their natural environment and isolated or separated from at least one other component with which they are naturally associated.

The PTEC Coding Sequences

The nucleic acid and deduced amino acid sequences of PTEC are shown in FIG. 1. In accordance with the invention, any nucleic acid sequence which encodes the amino acid sequence of PTEC can be used to generate recombinant molecules which express PTEC. In a specific embodiment described herein, the sequence for ptec was first isolated as Incyte Clone 836820 from a prostate cDNA library (PROSNOT07), Patent application Ser. No. 60/012,689, entitled "Polynucleotides and Polypeptides Derived from Human Prostate" by Stuart et al. and filed Feb. 27, 1996, the disclosure of which is incorporated herein by reference.

Methods for DNA sequencing are well known in the art and employ such enzymes as the Klenow fragment of DNA polymerase I, Sequenase® (US Biochemical Corp, Cleveland, Ohio)), Taq polymerase (Perkin Elmer, Norwalk, Conn.), thermostable T7 polymerase (Amersham, Chicago, Ill.), or combinations of recombinant polymerases and proofreading exonucleases such as the ELONGASE Amplification System marketed by Gibco BRL (Gaithersburg, Md.).

Methods to extend the DNA from an oligonucleotide primer annealed to the DNA template of interest have been developed for both single-stranded and double-stranded templates. Chain termination reaction products were separated using electrophoresis and detected via their incorporated, labeled precursors. Recent improvements in mechanized reaction preparation, sequencing and analysis have permitted expansion in the number of sequences that can be determined per day. Preferably, the process is automated with machines such as the Hamilton Micro Lab 2200 (Hamilton, Reno. Nev.), Peltier Thermal Cycler (PTC200; MJ Research, Watertown, Mass.) and the ABI 377 DNA sequencers (Perkin Elmer).

The quality of any particular cDNA library may be determined by performing a pilot scale analysis of the cDNAs and checking for percentages of clones containing vector, lambda or E. coli DNA, mitochondrial or repetitive DNA, and clones with exact or homologous matches to sequences in public databases.

Extending the Polynucleotide Sequence

The polynucleotide sequence of ptec may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using Oligo 4.0 (National Biosciences Inc, Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Parker JD et al (1991; Nucleic Acids Res 19:3055–60), teach walking PCR, a method for targeted gene walking which permits retrieval of unknown sequence. Promoter-Finder™ a new kit available from Clontech (Palo Alto, Calif.) uses PCR, nested primers and PromoterFinder libraries to walk in genomic DNA. This process avoids the need to screen libraries and is useful in finding intron/exon junctions.

Another PCR method, "Improved Method for Obtaining Full Length cDNA Sequences" by Guegler et al, patent application Ser. No. 08/487,112, filed Jun. 7, 1995 and hereby incorporated by reference, employs XL-PCR™ (Perkin Elmer) to amplify and extend nucleotide sequences.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension 5' of the coding region.

A new method for analyzing either the size or confirming the nucleotide sequence of sequencing or PCR products is capillary electrophoresis. Systems for rapid sequencing are available from Perkin Elmer, Beckman Instruments (Fullerton, Calif.), and other companies. Capillary sequencing employs flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (e.g. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez MC et al (1993) Anal Chem 65:2851–8).

Expression of the Nucleotide Sequence

In accordance with the present invention, polynucleotide sequences which encode PTEC, fragments of the polypeptide, fusion proteins or functional equivalents thereof may be used to generate recombinant DNA molecules that direct the expression of PTEC in appropriate host cells. Due to the inherent degeneracy of the genetic code, other DNA sequences which encode substantially the same or a functionally equivalent amino acid sequence, may be used to clone and express PTEC. As will be understood by those of skill in the art, it may be advantageous to produce PTEC-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of PTEC expression or to produce recombinant RNA transcripts having desirable properties, such as a longer half-life, than transcripts produced from naturally occurring sequence.

Also included within the scope of the present invention are polynucleotide sequences that are capable of hybridizing to the nucleotide sequence of FIG. 1 under conditions of intermediate to maximal stringency. Hybridization conditions are based on the melting temperature (Tm) of the nucleic acid binding complex or probe, as taught in Berger and Kimmel (1987, *Guide to Molecular Cloning Techniques,* Methods in Enzymology, Vol 152, Academic Press, San Diego, Calif.) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

The term "hybridization" as used herein shall include "any process by which a strand of nucleic acid joins with a complementary strand through base pairing" (Coombs J (1994) *Dictionary of Biotechnology,* Stockton Press, New York, N.Y.). Then by definition, hybridization includes the process of amplification as carried out in the polymerase chain reaction technologies described in Dieffenbach CW and GS Dveksler (1995, *PCR Primer, a Laboratory Manual,* Cold Spring Harbor Press, Plainview, N.Y.) and incorporated herein by reference.

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring ptec.

A "substitution" results from the replacement of one or more nucleotides or amino acids by different nucleotides or amino acids, respectively.

Altered ptec nucleic acid sequences which may be used in accordance with the invention include deletions, insertions or substitutions of different nucleotides resulting in a polynucleotide that encodes the same or a functionally equivalent PTEC. The protein may also show deletions, insertions or substitutions of amino acid residues which produce a silent change and result in a functionally equivalent PTEC. Deliberate amino acid substitutions may be made on the basis of similarity in polarity, charge, solubility, hydrophobicity, hydrophilicity, and/or the amphipathic nature of the residues as long as the biological activity of PTEC is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of ptec. As used herein, an "allele" or "allelic sequence" is an alternative form of ptec. Alleles result from a mutation, i.e., a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

The nucleotide sequences of the present invention can be engineered in order to alter a PTEC coding sequence for a variety of reasons, including but not limited to, alterations which modify the cloning, processing and/or expression of the gene product. For example, mutations may be introduced using techniques which are well known in the art, e.g., site-directed mutagenesis to insert new restriction sites, to alter glycosylation patterns, to change codon preference, to produce splice variants, etc.

In another embodiment of the invention, a natural, modified or recombinant ptec sequence may be ligated to a heterologous sequence to encode a fusion protein. For example, for screening of peptide libraries for inhibitors of PTEC activity, it may be useful to encode a chimeric PTEC protein that is recognized by a commercially available antibody. A fusion protein may also be engineered to contain a cleavage site located between a PTEC sequence and the heterologous protein sequence, so that the PTEC may be cleaved and purified away from the heterologous moiety.

In an alternate embodiment of the invention, the coding sequence of ptec could be synthesized, whole or in part, using chemical methods well known in the art (see Caruthers MH et al (1980) Nuc Acids Res Symp Ser 215–23, Horn T et al(1980) Nuc Acids Res Symp Ser 225–32, etc). Alternatively, the protein itself could be produced using chemical methods to synthesize a PTEC amino acid sequence, whole or in part. For example, peptide synthesis can be performed using various solid-phase techniques (Roberge JY et al (1995) Science 269:202–204) and automated synthesis may be achieved, for example, using the ABI 431A Peptide Synthesizer (Perkin Elmer) in accordance with the instructions provided by the manufacturer. The newly synthesized peptide can be purified by preparative high performance liquid chromatography (e.g., Creighton (1983) *Proteins, Structures and Molecular Principles,* WH Freeman and Co, New York, N.Y.). The composition of the synthetic peptides may be confirmed by amino acid analysis or sequencing (e.g., the Edman degradation procedure; Creighton, supra). Additionally the amino acid sequence of PTEC, or any part thereof, may be altered during direct synthesis and/or combined using chemical methods with sequences from other proteins, or any part thereof, to produce a variant polypeptide.

Expression Systems

In order to express a biologically active PTEC, the nucleotide sequence encoding PTEC or its functional equivalent, is inserted into an appropriate expression vector, i.e., a vector which contains the necessary elements for the transcription and translation of the inserted coding sequence.

Methods which are well known to those skilled in the art can be used to construct expression vectors containing a PTEC coding sequence and appropriate transcriptional or translational controls. These methods include in vitro recombinant DNA techniques, synthetic techniques and in vivo recombination or genetic recombination. Such techniques are described in Maniatis et al (1989) *Molecular Cloning, A Laboratory Manual,* Cold Spring Harbor Press, Plainview, N.Y. and Ausubel FM et al. (1989) *Current Protocols in Molecular Biology,* John Wiley & Sons, New York, N.Y.

A variety of expression vector/host systems may be utilized to contain and express a ptec coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1 (Gibco BRL) and ptrp-lac hybrids and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from the mammalian genes or from mammalian viruses are most appropriate. If it is necessary to generate a cell line that contains multiple copies of ptec, vectors based on SV40 or EBV may be used with an appropriate selectable marker.

In bacterial systems, a number of expression vectors may be selected depending upon the use intended for PTEC. For example, when large quantities of PTEC are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the ptec coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a PTEC coding sequence may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi RM (1991) Results Probl Cell Differ 17:85–105) may be used. These constructs can be introduced into plant cells by direct DNA transformation or pathogen-mediated transfection. For reviews of such techniques, see Hobbs S or Murry LE in McGraw Yearbook of Science and Technology (1992) McGraw Hill New York, N.Y., pp 191–196 or Weissbach and Weissbach (1988) Methods for Plant Molecular Biology, Academic Press, New York, N.Y., pp 421–463.

An alternative expression system which could be used to express ptec is an insect system. In one such system, *Autographa californica* nuclear polyhedrosis virus (AcNPV) is used as a vector to express foreign genes in *Spodoptera frugiperda* cells or in Trichoplusia larvae. The ptec coding sequence may be cloned into a nonessential region of the virus, such as the polyhedrin gene, and placed under control of the polyhedrin promoter. Successful insertion of ptec will render the polyhedrin gene inactive and produce recombinant virus lacking coat protein coat. The recombinant viruses are then used to infect *S. frugiperda* cells or Trichoplusia larvae in which PTEC is expressed (Smith et al (1983) J Virol 46:584; Engelhard EK et al (1994) Proc Nat Acad Sci 91:3224–7).

In mammalian host cells, a number of viral-based expression systems may be utilized. In cases where an adenovirus is used as an expression vector, a ptec coding sequence may be ligated into an adenovirus transcription/translation complex consisting of the late promoter and tripartite leader sequence. Insertion in a nonessential E1 or E3 region of the viral genome will result in a viable virus capable of expressing PTEC in infected host cells. (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a ptec sequence. These signals include the ATG initiation codon and adjacent sequences. In cases where ptec, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express ptec may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman SC and RC Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes CA et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the ptec is inserted within a marker gene sequence, recombinant cells containing ptec can be identified by the absence of marker gene function. Alternatively, a marker gene can be placed in tandem with a PTEC sequence under the control of a single promoter. Expression of the marker gene in response to induction or selection usually indicates expression of the tandem ptec as well.

Alternatively, host cells which contain the coding sequence for ptec and express PTEC may be identified by a variety of procedures known to those of skill in the art.

These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the ptec polynucleotide sequence can be detected by DNA-DNA or DNA-RNA hybridization or amplification using probes, portions or fragments of ptec. Nucleic acid amplification based assays involve the use of oligonucleotides or oligomers based on the ptec sequence to detect transformants containing ptec DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

The expression of an MCP-4 protein product can be assessed biologically in a chemotaxis or Ca++ mobilization assay or immunologically in Western blot, enzyme-linked immunoassays (ELISA) and the like.

Falk WR et al (1980, J Immunol Methods 33:239) first described the assessment of chemotactic activity using 48-well microchemotaxis chambers. In this assay, the expressed chemokine is placed in media on one side of a polycarbonate filter and a particular population of cells is suspended in the same media on the opposite side of the filter. Sufficient incubation time allows the cells to traverse the filter in response to the chemokine concentration gradient. Filters are recovered from each well, and the cells adhering to the side of the filter facing the chemokine are typed and quantified.

Populations of cells used in such assays may include blood cells obtained from venipuncture or enriched populations of neutrophils, peripheral blood mononuclear cells, monocytes and lymphocytes obtained by density gradient centrifugation and/or negative selection using antibodies specific for surface molecules of the nondesired population. For example, incubating a population of T lymphocytes with CD4+ and separating out CD4+bound cells may result in a CD8+ enriched T-lymphocyte population.

To assay non-chemotactic activity of PTEC, testing may involve measurement of mobilization of $Ca^{++}$ and comparison of the results with standard measurements. The assay for mobilization of $Ca^{++}$ as part of the signal transduction pathway requires preloading monocytes with a fluorescent probe whose emission characteristics have been altered by $Ca^{++}$ binding. When the cells are exposed to an activating stimulus, $Ca^{++}$ flux is determined by observation of the cells in a fluorometer. The measurement of $Ca^{++}$ mobilization has been described in Grynkievicz G et al (1985) J Biol Chem 260:3440, and McColl S et al (1993) J Immunol 150:4550–4555, incorporated herein by reference. Another measure of monocyte activation is the assay for adhesion molecule expression in lymphocytes (Jiang Y et al (1992) J Immunol 148: 2423–8; Taub D et al (1993) Science 260: 355–358).

A variety of protocols for detecting and measuring the expression of PTEC, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on PTEC is preferred, but a competitive binding assay may be employed. These and other assays are described, among other places, in Hampton R et al (1990, Serological Methods, a Laboratory Manual, APS Press, St Paul, Minn.) and Maddox DE et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to ptec include oligolabeling, nick translation, end-labeling or PCR amplification using a labeled nucleotide. Alternatively, the ptec sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway, N.J.), Promega (Madison, Wis.), and US Biochemical Corp (Cleveland, Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of PTEC

Host cells transformed with a PTEC nucleotide sequence may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing ptec can be designed with signal sequences which direct secretion of PTEC through a prokaryotic or eukaryotic cell membrane. Other recombinant constructions may join ptec to nucleotide sequence encoding a polypeptide domain which will facilitate purification of soluble proteins (Kroll DJ et al (1993) DNA Cell Biol 12:441–53; cf discussion of vectors infra containing fusion proteins).

PTEC may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of cleavable linker sequences such as Factor XA or enterokinase (Invitrogen, San Diego, Calif.) between the purification domain and PTEC is useful to facilitate purification.

Uses of PTEC

The rationale for diagnostic and therapeutic uses of PTEC sequences is based on the disclosed nucleic acid and amino acid sequences, the homology between PTEC, RANTES and MIP-1α (FIGS. 2 and 3), and the presence of the ptec transcript in the PROSNOT07 cDNA library.

The nucleic acid sequence (SEQ ID NO:1), its complement, fragments or oligomers, and anti-PTEC antibodies may be used as diagnostic compositions to assay bodily fluids or extracts of biological samples for expression of ptec. Purified polynucleotides and polypeptides can be used as positive controls in their respective nucleic acid or protein based assays to validate and quantitate the expression of ptec either during preliminary diagnosis or during the course of therapeutic treatment for a particular condition or disease.

The nucleic acid sequence, its complement, fragments or oligomers, and anti-PTEC antibodies are useful in evaluating disease associated expression of ptec. Activation or excessive proliferation of leukocytes, particularly monocytes, macrophages, eosinophils, basophils, mast and T cells have been associated with conditions or diseases such as viral, bacterial, fungal or helminthic infections; allergic or asthmatic responses; mechanical injury associated with trauma; arteriosclerosis, atherogenesis or collagen vascular diseases; autoimmune diseases such as rheumatoid arthritis, myasthenia gravis, systemic lupus erythematosus, diabetes or hemolytic anemia; and leukemia, lymphomas or carcinomas. For example, the expression of ptec in the prostate tissue removed from the 69 year old male suggests that the naturally occurring protein was being expressed and secreted in association with adenocarcinoma, benign prostatic hypertrophy, and/or associated infection.

PTEC as a RANTES homolog would appear to be intimately associated in the diseases of immediate type hypersensitivity such as allergy, asthma, rhinitis, urticaria, and dermatitis triggered by IgE interaction with cell surface receptors. Receptor perturbation on basophils and mast cells (in tonsils, adenoids, nasal polyps or skin) activates mobilization of intracellular calcium ions and results in the release of secretory granules, formation of bioactive lipid mediators and platelet-activating factor. The recombinant nucleotides and proteins of the instant application provide the ability to regulate the activity of PTEC in immediate hypersensitive reactions.

Purified recombinant protein can be administered to immuno-compromised individuals specifically to stimulate T lymphocyte proliferation. Immune deficiency diseases include but are not limited to AIDS, X-linked agammaglobulinemia, ataxia telangiectasia, cirrhosis, cystic fibrosis, diabetes mellitus, hepatitis, and sickle cell diseases.

Purified nucleic acid sequences, antisense molecules, PNAs, purified protein, antibodies, antagonists or inhibitors can all be used as pharmaceutical compositions. Delivery of these molecules for therapeutic purposes is further described under Pharmaceutical Compositions. The most appropriate therapy depends on the patient, the specific diagnosis, and the physician who is treating and monitoring the patient's condition.

PTEC Antibodies

Procedures well known in the art can be used for the production of antibodies to PTEC. Such antibodies include, but are not limited to, polyclonal, monoclonal, chimeric, single chain, Fab fragments and fragments produced by a Fab expression library. Neutralizing antibodies, i.e., those which inhibit dimer formation, are especially preferred for diagnostics and therapeutics.

For the production of antibodies, various hosts including goats, rabbits, rats, mice, etc may be immunized by injection with PTEC or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to PTEC may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York, N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce PTEC-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for PTEC may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse WD et al (1989) Science 256:1275–1281).

PTEC-specific antibodies are useful for the diagnosis of conditions and diseases associated with expression of PTEC. A variety of protocols for competitive binding or immunoradiometric assays using either polyclonal or monoclonal antibodies with established specificities are well known in the art. Such immunoassays typically involve the formation of complexes between PTEC and its specific antibody and the measurement of complex formation. A two-site, monoclonal-based immunoassay utilizing monoclonal antibodies reactive to two noninterfering epitopes on a specific PTEC protein is preferred, but a competitive binding assay may also be employed. These assays are described in Maddox DE et al (1983, J Exp Med 158:1211).

Diagnostic Assays Using PTEC Specific Antibodies

Particular PTEC antibodies are useful for the diagnosis of conditions or diseases characterized by induced expression of PTEC or in assays to monitor patients being treated with PTEC or with antagonists or inhibitors of PTEC. Diagnostic assays for PTEC include methods utilizing the antibody and a label to detect PTEC in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring PTEC, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on PTEC is preferred, but a competitive binding assay may be employed. These assays are described, among other places, in Maddox, DE et al (1983, J Exp Med 158:1211).

In order to provide a basis for diagnosis, normal or standard values for PTEC expression must be established. This is accomplished by combining body fluids or cell extracts taken from normal subjects, either animal or human, with antibody to PTEC under conditions suitable for complex formation which are well known in the art. The amount of standard complex formation may be quantified by comparing it with a dilution series of purified PTEC as a positive control, where known amounts of antibody are combined with known concentrations of purified PTEC . Then, standard values obtained from normal samples may be compared with values obtained from samples from subjects potentially affected by disease. Deviation between standard and subject values establishes the presence of disease state.

Drug Screening

PTEC, its catalytic or immunogenic fragments or oligopeptides, can be used for screening therapeutic compounds in any of a variety of drug screening techniques. The fragment employed in such a test may be free in solution, affixed to a solid support, borne on a cell surface, or located intracellularly. The formation of binding complexes, between PTEC and the agent being tested, may be measured.

Another technique for drug screening which provides for high throughput screening of compounds having suitable binding affinity to the PTEC is described in detail in "Determination of Amino Acid Sequence Antigenicity" by Geysen HN, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of PTEC and washed. Bound PTEC is then detected by methods well known in the art. Purified PTEC can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding PTEC specifically compete with a test compound for binding PTEC. In this manner, the antibodies can be used to detect the presence of any peptide which shares one or more antigenic determinants with PTEC.

Uses of the Polynucleotide Encoding PTEC

A polynucleotide, ptec, or any part thereof, may be used for diagnostic and/or therapeutic purposes. For diagnostic purposes, the ptec of this invention may be used to detect and quantitate gene expression in biopsied tissues in which PTEC activity may be implicated. The diagnostic assay is useful to distinguish between normal and excess expression of ptec and to monitor regulation of ptec levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding PTEC or closely related molecules. The specificity of the probe, whether it is made from a highly conserved region, e.g., 10 unique nucleotides in the 5' regulatory region, or a less conserved region, e.g., between cysteine residues especially in the 3' region, and the stringency of the hybridization or amplification (high, intermediate or low) will determine whether the probe identifies only naturally occurring ptec, alleles or related sequences.

Diagnostics

Polynucleotide sequences encoding PTEC may be used for the diagnosis of conditions or diseases with which the expression of PTEC is associated. For example, polynucleotide sequences encoding PTEC may be used in hybridization or PCR assays of fluids or tissues from biopsies to detect ptec expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

Such assays may be also be used to evaluate the efficacy of a particular therapeutic treatment regime in animal studies, in clinical trials, or in monitoring the treatment of an individual patient. In order to provide a basis for the diagnosis of disease, a normal or standard profile for ptec expression must be established. This is accomplished by combining body fluids or cell extracts taken from normal subjects, either animal or human, with ptec, or a portion thereof, under conditions suitable for hybridization or amplification. Standard hybridization may be quantified by comparing the values obtained for normal subjects with a dilution series of ptec run in the same experiment where a known amount of purified ptec is used. Standard values obtained from normal samples may be compared with values obtained from samples from cachectic subjects affected by ptec expression. Deviation between standard and subject values establishes the presence of disease.

Once disease is established, a therapeutic agent is administered; and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR as described in U.S. Pat. Nos. 4,683,195 and 4,965,188 provides additional uses for oligonucleotides based upon the ptec sequence. Such oligomers are generally chemically synthesized, but they may be generated enzymatically or produced from a recombinant source. Oligomers generally comprise two nucleotide sequences, one with sense orientation (5'—>3') and one with antisense (3'<—5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods to quantitate the expression of a particular molecule include radiolabeling (Melby PC et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. For example, the presence of ptec in extracts of biopsied tissues may indicate the onset of adenocarcinoma. A definitive diagnosis of this type may allow health professionals to begin aggressive treatment and prevent further worsening of the condition. Similarly, further assays can be used to monitor the progress of a patient during treatment.

Therapeutics

The polynucleotide disclosed herein may be useful in the treatment of various hypersensitive or immune conditions or diseases. By introducing the antisense molecules (anti-ptec) into suspect cancerous cells, gene therapy can be used to reduce or eliminate PTEC expression. In such instances, flooding the cell with an antisense molecule prevents translation of the amino acid sequence.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express anti-ptec. See, for example, the techniques described in Maniatis et al (supra) and Ausubel et al (supra).

The polynucleotides comprising full length cDNA sequence and/or its regulatory elements enable researchers to use ptec as an investigative tool in sense (Youssoufian H and HF Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding PTEC can be turned off by transfecting a cell or tissue with expression vectors which express high levels of the desired fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of ptec, i.e., the promoters, enhancers, and introns. Oligonucleotides derived from the transcription initiation site, e.g., between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee JE et al. (In: Huber BE and BI Carr (1994) *Molecular and Immunologic Approaches,* Futura Publishing Co, Mt Kisco, N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of ptec.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding PTEC. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient, as presented in U.S. Pat. Nos. 5,399,493 and 5,437,994, disclosed herein by reference. Delivery by transfection and by liposome are quite well known in the art.

Furthermore, the nucleotide sequences for ptec disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for ptec can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price CM (1993; Blood Rev 7:127–34) and Trask BJ (1991; Trends Genet 7:149–54).

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson TJ et al. (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention comprises pharmaceutical compositions which may comprise nucleotides, proteins, antibodies, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that is well known in the art, e.g., by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of PTEC, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, e.g., tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; and 5,225,212. Those skilled in the art will employ different formulations for nucleotides than for proteins or their inhibitors. Similarly, delivery of polynucleotides or polypeptides will be specific to particular cells, conditions, locations, etc.

It is contemplated PTEC can be expressed and delivered in a suitable formulation to stimulate T lymphocyte proliferation in immuno-compromised individuals. In a clinical setting, the rigorous monitoring of PTEC levels allows the attending physician to adjust PTEC levels in a range which promotes proliferation and avoids other cytokine associated problems such as toxic shock syndrome. Similarly, administration of antagonists or inhibitors of PTEC and monitoring of an infected or cancer patient should minimize undesired side effects.

The examples below are provided to illustrate the subject invention and are not included for the purpose of limiting the invention.

EXAMPLES

I—Prostate CDNA Library Construction

The full length gene ptec from Incyte Clone No 836820 was identified among the cDNAs isolated from a prostate library (PROSNOT07). The PROSNOT07 cDNA library was made from non-tumorous prostate tissue removed from a 69-year-old male (specimen #0182B; Mayo Clinic, Rochester, Minn.). The pathology report indicated that the patient had an adenocarcinoma (Gleason grade 3+4).

The frozen tissue was homogenized using a Brinkmann Homogenizer Polytron PT-3000 (Brinkmann Instruments, Westbury, N.J.) and lysed immediately in a buffer containing guanidinium isothiocyanate. The lysate was then loaded on a 5.7M CsCl cushion and ultracentrifuged in an SW28 swinging bucket rotor on a Beckman L8-70M Ultracentrifuge (Beckman Instruments) for 18 hours at 25,000 rpm at ambient temperature. The RNAs were extracted with phenol chloroform pH 4.0, precipitated using 0.3M sodium acetate and 2.5 volumes of ethanol, resuspended in DEPC-treated water and DNase treated at 37° C. The RNAs were re-extracted with phenol chloroform pH 4.0 and precipitated using sodium acetate and ethanol. The RNA was isolated using the Qiagen Oligotex kit (QIAGEN Inc, Chatsworth, Calif.).

The RNA was handled according to the recommended protocols in the SuperScript Plasmid System for cDNA Synthesis and Plasmid Cloning (catalog #18248-013; Gibco/BRL, Gaithersburg, Md.). cDNAs were fractionated on a Sepharose CL4B column (catalog #275105, Pharmacia), and those cDNAs exceeding 400 bp were ligated into pSport I. The plasmid pSport I was subsequently transformed into DH5a™ competent cells (Cat. #18258-012, Gibco/BRL).

II—Isolation and Sequencing of cDNA Clones

Plasmid DNA was released from the cells and purified using the REAL Prep 96 Plasmid Kit for Rapid Extraction Alkaline Lysis Plasmid Minipreps (Catalog #26173; QIAGEN, Inc). This kit enables the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) the cultures were incubated for 19 hours after the wells were inoculated and then lysed with 0.3 ml of lysis buffer; and 3) following isopropanol precipitation, the plasmid DNA pellet was resuspended in 0.1 ml of distilled water. After the last step in the protocol, samples were transferred to a Beckman 96-well block for storage.

The cDNAs were sequenced by the method of Sanger F and AR Coulson (1975; J Mol Biol 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III—Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul SF (1993) J Mol Evol 36:290–300; Altschul, SF et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV—Extension of PTEC to Recover Regulatory Elements

The nucleic acid sequence of full length PTEC (SEQ ID NO:1) may be used to design oligonucleotide primers for obtaining 5' sequences from genomic libraries. One primer is synthesized to initiate extension in the antisense direction (XLR) and the other is synthesized to extend sequence in the sense direction (XLF). The primers allowed the known PTEC sequence to be extended "outward" generating amplicons containing new, unknown nucleotide sequence for the control region of interest. The initial primers may be designed from the cDNA using Oligo 4.0 (National Biosciences Inc, Plymouth, Minn.), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

A human genomic library is used to extend and amplify 5' upstream sequence. If necessary, a second set of primers is designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown, Mass.) and the following parameters:

| Step 1  | 94° C. for 1 min (initial denaturation) |
|---------|------------------------------------------|
| Step 2  | 65° C. for 1 min                         |
| Step 3  | 68° C. for 6 min                         |
| Step 4  | 94° C. for 15 sec                        |
| Step 5  | 65° C. for 1 min                         |
| Step 6  | 68° C. for 7 min                         |
| Step 7  | Repeat step 4–6 for 15 additional cycles |
| Step 8  | 94° C. for 15 sec                        |
| Step 9  | 65° C. for 1 min                         |
| Step 10 | 68° C. for 7:15 min                      |
| Step 11 | Repeat step 8–10 for 12 cycles           |
| Step 12 | 72° C. for 8 min                         |
| Step 13 | 4° C. (and holding)                      |

A 5–10 μl aliquot of the reaction mixture is analyzed by electrophoresis on a low concentration (about 0.6–0.8%) agarose mini-gel to determine which reactions were successful in extending the sequence. The largest products or bands were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent *E. coli* cells (in 40 μl of appropriate media) are transformed with 3 μl of ligation mixture and cultured in 80 μof SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94° C. for 60 sec                            |
|--------|----------------------------------------------|
| Step 2 | 94° C. for 20 sec                            |
| Step 3 | 55° C. for 30                                |
| Step 4 | 72° C. for 90 sec                            |
| Step 5 | Repeat steps 2–4 for an additional 29 cycles |
| Step 6 | 72° C. for 180 sec                           |
| Step 7 | 4° C. (and holding)                          |

Aliquots of the PCR reactions are run on agarose gels together with molecular weight markers. The sizes of the PCR products are compared to the original partial cDNAs, and appropriate clones are selected, ligated into plasmid and sequenced.

V—Labeling of Hybridization Probes

Hybridization probes derived from SEQ ID NO:1 may be employed to screen cDNAs, mRNAs or genomic DNAs. Although the labeling of oligonucleotides, consisting of about 20 base-pairs, is specifically described, essentially the same procedure may be used with larger cDNA fragments. Oligonucleotides are labeled by combining 50 pmol of each oligomer and 250 mCi of [$\gamma$-$^{32}$P] adenosine triphosphate (Amersham, Chicago, Ill.) and T4 polynucleotide kinase (DuPont NEN®, Boston, Mass.). The labeled oligonucleotides are purified with Sephadex G-25 super fine resin column (Pharmacia). A portion containing $10^7$ counts per minute of each is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VI—Antisense Molecules

The PTEC sequence, or any part thereof, may be used to inhibit in vivo or in vitro expression of native PTEC. Although use of antisense oligonucleotides, consisting of about 20 base-pairs, is specifically described, essentially the same procedure may be used with larger cDNA fragments. An oligonucleotide based on the coding sequence of PTEC as shown in FIG. 1 may be used to inhibit expression of native PTEC. The complementary oligonucleotide can be designed from conserved 5' sequence as shown in FIG. 2 and used either to inhibit transcription by preventing promoter binding to the upstream nontranslated sequence or translation of an PTEC transcript by preventing the ribosome from binding. Using an appropriate portion of the leader and 5' sequence of SEQ ID NO:1, an effective antisense oligonucleotide would include approximately codons $A_{46}$ to $T_{72}$ spanning the region which translates the residues $S_{16}$ to $R_{24}$ of the polypeptide and shown in FIG. 1.

VII—Expression of PTEC

Expression of the PTEC may be accomplished by subcloning the cDNAs into appropriate vectors and transfecting the vectors into host cells. In this case, the cloning vector, pBluescript, previously used for the generation of the cDNA library is used to express PTEC in *E. coli*. Upstream of the cloning site, this vector contains a promoter for $\beta$-galactosidase, followed by sequence containing the amino-terminal Met and the subsequent 7 residues of $\beta$-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of $\beta$-galactosidase, about 5 to 15 residues of linker, and the full length PTEC. The signal sequence directs the secretion of PTEC into the bacterial growth media which can be used directly in the following assay for activity.

VIII—PTEC Activity

Chemokine chemotactic activity is usually measured in 48-well microchemotaxis chambers (Falk, supra). In each well, two compartments are separated by a filter that allows the passage of cells from one compartment into the other in response to a chemical gradient. Cell culture medium into which PTEC has been secreted is placed on one side of a polycarbonate filter, and peripheral blood cells are suspended in the same media on the opposite side of the filter. Sufficient incubation time is allowed for the cells to traverse the filter in response to diffusion and resulting concentration gradient of PTEC. Filters are recovered from each well, and specific cell types, e.g., monocytes, adhering to the side of the filter facing the chemokine are identified and counted.

Cell specificity may be determined by performing the assay on fractionated populations of cells such as enriched populations of neutrophils, mononuclear cells, or lymphocytes obtained by density gradient centrifugation. Specific T lymphocyte populations can be purified using CD8+ and CD4+ specific antibodies for negative selection.

IX—Production of PTEC Specific Antibodies

Although PTEC purified using PAGE electrophoresis (Maniatis, supra) can be used to immunize rabbits using standard protocols, a monoclonal approach is more commonly employed. The amino acid sequence translated from PTEC is analyzed using DNASTAR software (DNASTAR Inc) to determine regions of high immunogenicity and a corresponding oligopolypeptide is synthesized and used to raise antibodies by means known to those of skill in the art. Analysis to select appropriate epitopes, such as those near the C-terminus or in adjacent hydrophilic regions is described by Ausubel FM et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel FM et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

X—Purification of Native PTEC Using Specific Antibodies

Native or recombinant PTEC can be purified by immunoaffinity chromatography using antibodies specific for PTEC. An immunoaffinity column is constructed by covalently coupling PTEC antibody to an activated chromatographic resin such as CnBr-activated Sepharose (Pharmacia Biotech). After the coupling, the resin is blocked and washed according to the manufacturer's instructions.

Media containing PTEC is passed over the immunoaffinity column, and the column is washed under conditions that allow the preferential absorbance of PTEC (e.g., high ionic strength buffers in the presence of detergent). The column is eluted under conditions that disrupt antibody/PTEC binding (e.g., a buffer of pH 2–3 or a high concentration of a chaotrope such as urea or thiocyanate ion), and PTEC is collected.

XI—Identification of Molecules Which Interact with PTEC

PTEC, or biologically active fragments thereof, are labelled with $^{125}$I Bolton-Hunter reagent (Bolton, AE and Hunter, WM (1973) Biochem J 133: 529). Candidate molecules previously arrayed in the wells of a 96 well plate are incubated with the labelled PTEC, washed and any wells with labelled PTEC complex are assayed. Data obtained using different concentrations of PTEC are used to calculate values for the number, affinity, and association of PTEC with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A purified polynucleotide encoding a polypeptide with an amino acid sequence shown in SEQ ID NO:2.

2. The polynucleotide of claim 1 wherein the nucleic acid sequence consists of SEQ ID NO:1, or its complement.

3. An expression vector comprising the polynucleotide of claim 1.

4. A host cell transformed with the expression vector of claim 3.

5. A method for producing a polypeptide comprising the amino acid sequence shown in SEQ ID NO:2, the method comprising the steps of:

a) culturing the host cell of claim 3 under conditions suitable for the expression of the polypeptide; and b) recovering the polypeptide from the host cell culture.

* * * * *